United States Patent [19]

Fujikake et al.

[11] Patent Number: 4,821,575
[45] Date of Patent: Apr. 18, 1989

[54] ULTRASONIC FLAW DETECTING METHOD AND APPARATUS

[75] Inventors: Yoichi Fujikake, Kawasaki; Takao Sugimoto, Kimitsu; Kiyohide Tamaki, Fuchu; Yoshio Udagawa, Higashiosaka, all of Japan

[73] Assignee: Nippon Steel Corporation, Chiyoda, Japan

[21] Appl. No.: 105,118

[22] Filed: Oct. 5, 1987

[30] Foreign Application Priority Data

Oct. 6, 1986 [JP] Japan ................................ 61-237722

[51] Int. Cl.⁴ ............................................. G01N 29/04
[52] U.S. Cl. ........................................ 73/626; 73/628
[58] Field of Search .................. 73/622, 625, 626, 628

[56] References Cited

U.S. PATENT DOCUMENTS

| | | | |
|---|---|---|---|
| 4,160,386 | 7/1979 | Jackson | 73/625 |
| 4,195,530 | 4/1980 | Ross et al. | 73/638 |
| 4,206,511 | 6/1980 | Ries et al. | 73/625 |
| 4,660,419 | 4/1987 | Derkacs et al. | 73/622 |

FOREIGN PATENT DOCUMENTS

| | | | |
|---|---|---|---|
| 0154005 | 9/1982 | Japan | 73/622 |
| 62-194454 | 8/1987 | Japan | |
| 62-194455 | 8/1987 | Japan | |

*Primary Examiner*—Michael J. Tokar
*Assistant Examiner*—Lawrence G. Fess

[57] ABSTRACT

A method for ultrasonically detecting flaws in a welded portion of a pipe by using an ultrasonic wave phased array probe having an array of a plurality of transducer elements for emitting and receiving ultrasonic wave beams, wherein at least one monitoring probe is located in the vicinity of the welded portion to receive the ultrasonic wave beam, whereby peak values of the ultrasonic wave beams are detected within a predetermined gate, a maximum peak value of the detected peak values is determined to determine a pilot beam having the maximum peak value, and effective beams which reach the portion of the welding portion to be tested are determined from the determined pilot beam.

10 Claims, 13 Drawing Sheets

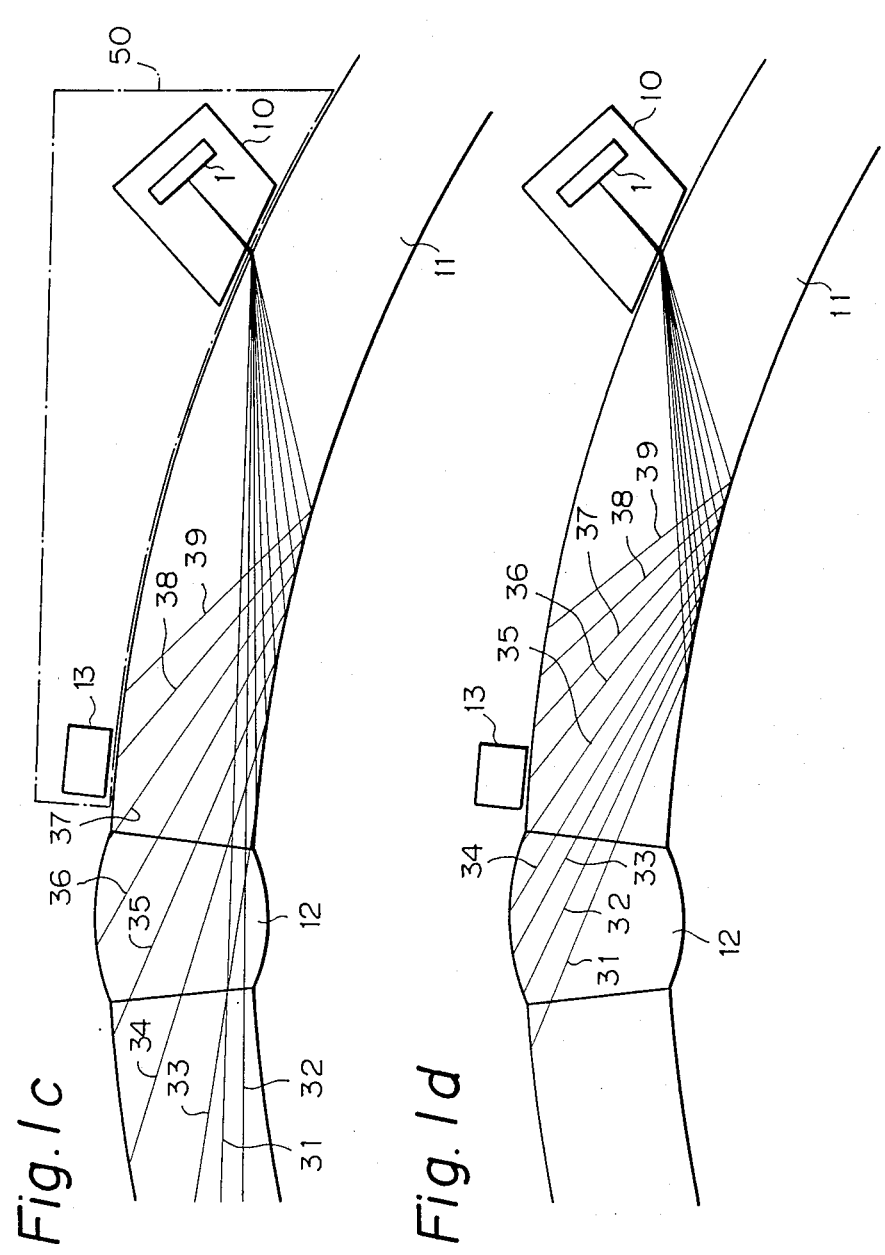

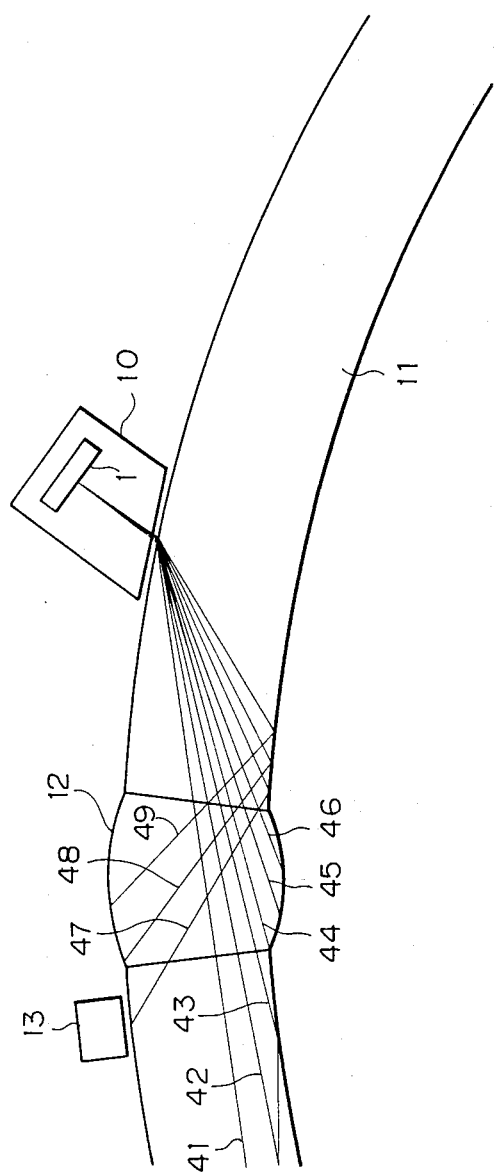

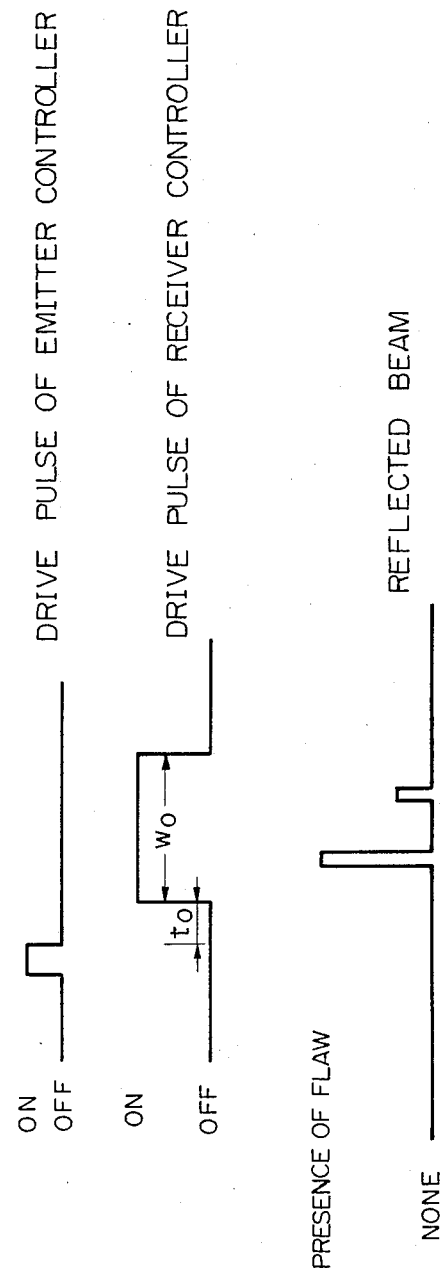

ULTRASONIC FLAW DETECTING METHOD AND APPARATUS

BACKGROUND OF THE INVENTION

1. Field of the Invention

The present invention relates to a method and apparatus for the ultrasonic detection of flaws in a welded portion of, for example, a steel UO pipe.

In a well known method of nondestructive ultrasonic testing of objects such as pipes, in which an ultrasonic beam is passed through an object to be tested by a transducer, reflections of echoes from an internal structure of the object are detected to determine the characteristics of that internal structure.

More precisely, a piezoelectric crystal is subjected to a pulse by an electrical energy signal, which causes an ultrasonic wave beam to be emitted. It is also known that, if the ultrasonic wave beam passed through the object is reflected by a flaw and returned to the piezoelectric crystal along the same path as it is emitted, the crystal responds by producing an electric signal. Therefore, it is possible to detect flaws in the internal structure of an object by detecting the electric signals produced by the crystal.

2. Description of the Related Art

When a UO-steel pipe is produced by first bending a steel flat plate into a U-shape and then bending the U-shaped plate into an O-shape, and finally welding the butt ends of the O-shaped pipe, the resultant UO-steel pipe must be tested to detect possible flaws in the internal structure of the welded portions thereof. Generally, the plate blank itself is tested before U-and O-shaping operations.

In a conventional ultrasonic flaw detecting process, the control of, for example, the angle at which the ultrasonic beam is passed through the object, and the relevant arithmetic process in a computer (central processing unit) etc., are effected on the supposition that the steel pipe has a completely circular cross section.

However, it is almost impossible to produce a pipe, especially a UO-pipe, which is completely circular, and this non-circularity of the pipe to be tested impairs the accuracy of the detection process. Nevertheless, in the prior art, no measures have been disclosed to counteract the effects of this non- circularity.

SUMMARY OF THE INVENTION

The primary object of the present invention is, therefore, to provide an ultrasonic detection method and apparatus for accurately detecting flaws particularly in a welded portion of a pipe by counteracting any irregularity of roundness of the pipe.

Still another object of the present invention is to provide an ultrasonic detection method and apparatus for precisely detecting flaws in a pipe even if the inclination angle of a probe (transducer) is deviated from a designed location with respect to a pipe to be tested.

To achieve the above objects, according to the present invention, there is provided an ultrasonic detection method for the ultrasonic detection of flaws in a portion of a subject to be tested by using an ultrasonic wave phased array probe having an array of a plurality of transducers for emitting and receiving ultrasonic wave beams in a sector scanning fashion in which the beams are scanned substantially in the form of a sector, and wherein at least one monitoring probe is located in the vicinity of the portion of the subject to be tested by the ultrasonic wave beams, comprising detecting peak values of the ultrasonic wave beams within a predetermined gate, determining a maximum peak value of the detected peak values to determine a pilot beam having the maximum peak value, determining from the determined pilot beam effective beams which reach the portion to be tested, so that the detection of flaws can be effected by using only the effective beams.

According to another aspect of the present invention, there is provided an apparatus for the ultrasonic detection of flaws in a portion of a subject to be tested, by using an ultrasonic wave phased array probe having an array of a plurality of transducers for emitting and receiving ultrasonic wave beams in a sector scanning fashion in which the beams are scanned substantially in the form of a sector, comprising a monitoring probe which is located in the vicinity of the portion to be tested by the ultrasonic wave beams.

According to still another aspect of the present invention, the apparatus further comprises means for detecting peak values of the ultrasonic wave beams within a predetermined gate, means for determining a maximum peak value of the detected peak values to determine a pilot beam having the maximum peak value, and means for determining from the detected pilot beam effective beams which reach the portion to be tested.

With the above arrangement of the present invention, since the fluctuation of the direction of the ultrasonic wave beams, i.e., the fluctuation of the refraction angles of the beams propagated in the subject, due to the irregularity of the subject to be tested and the inclination of the array type probe, are always monitored by the monitoring probe, only the data of the effective beams which actually reach the portion to be tested are used to detect the flaws in that portion, and accordingly, an accurate and more certain detection of flaws can be achieved.

BRIEF DESCRIPTION OF THE DRAWINGS

The invention will be described below in detail with reference to the accompanying drawings, in which:

FIGS. 1a to 1i show embodiments of the present invention, wherein: FIG. 1a is a schematic view of an ultrasonic detection apparatus of the present invention, FIG. 1b is an enlarged view of a part of FIG. 1a, showing the paths of ultrasonic wave beams, FIG. 1c is a schematic view showing deviations in the paths of the beams caused by a fluctuation of the inclination of a probe shown in FIG. 1a, FIG. 1d is a schematic view showing deviations of the beams caused by the fluctuation of the inclination of a probe in the opposite direction to that of FIG. 1c, FIG. 1e is a schematic view of another embodiment of the present invention, in which two monitoring probes are provided, FIG. 1f is a schematic view of still another embodiment of the present invention, FIG. 1g is a flow chart for carrying out the detection of flaws according to the present invention, FIG. 1h is a timing chart of the drive pulses of a transmitter controller, drive pulses of a receiver controller, and the reflected beams, by way of an example, and FIG. 1i is a flow chart for carrying out the detection of flaws corresponding to the arrangement shown in FIG. 1e;

DESCRIPTION OF THE PREFERRED EMBODIMENTS

Figure 2:
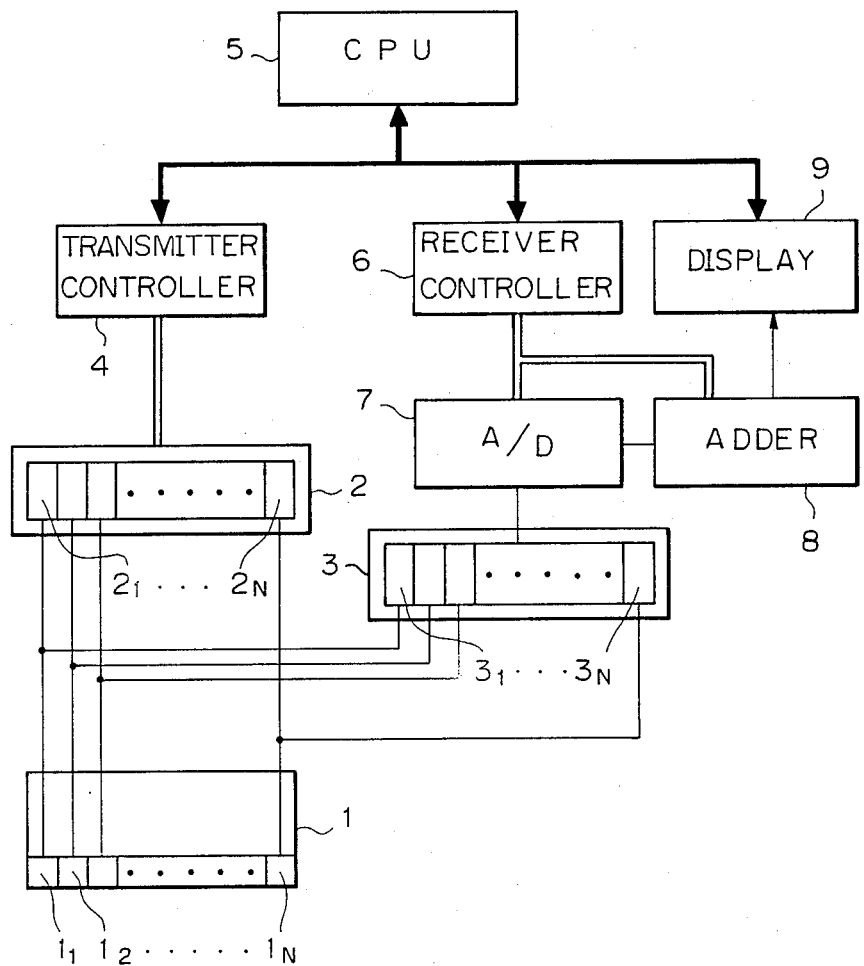
FIG. 2 is a view showing a known phased array ultrasonic testing apparatus.

FIG. 2 shows a known phased array ultrasonic testing equipment disclosed, for example, in Japanese Unexamined Patent Publication (Kokai) No. 57-147053, in which an array (probe) of n-channels of transducer elements (vibrators) $1_1, 1_2, \ldots 1_n$, which are in the form of an elongated piece having a narrow width, are electrically connected to an ultrasonic wave transmitter unit 2 having a group of n-channels of transmitters $2_1, 2_2, \ldots 2_n$, and a wave receiver unit 3 having a group of n-channels of ultrasonic receivers $3_1, 3_2, \ldots 3_n$.

The transmitter unit 2 is electrically connected to an transmitter controller 4 which outputs trigger signals to the transmitter unit 2 to enable the transmitters $2_1, 2_2, \ldots 2_n$ to generate pulses. The transmitter controller 4 is electrically connected to a computer 5 which incorporates programs for controlling the channels of the transmitters to be actuated to produce ultrasonic waves, and the delay times between the transmitters The deflection angle (steered angle) of a desired ultrasonic wave which is produced, for example, by a plurality of transducer elements to which transmitted pulses are successively given at predetermined delay times by the transmitters $2_1, 2_2, \ldots 2_n$, can be determined by the delay time. The delay time must be determined by also taking a distance of convergence of the ultrasonic wave into consideration.

The reflected ultrasonic waves are received by the transducer elements $1_1, 1_2, \ldots 1_n$, and the transducer elements output pulse voltages to the receivers $3_1, 3_2, \ldots 3_n$ of the receiver unit 3. The N-signals of the receiver unit 3 are converted to digital signals by an analog-digital converter 7 (A/D converter) after amplification. When the analog signals from the ultrasonic wave receivers $3_1, 3_2, \ldots 3n$ are converted to digital signals, the time at which the conversion is commenced is varied in accordance with the delay times mentioned above.

The digital signals are input to an adder 8 in which channels of the receivers $3_1, 3_2, \ldots 3_n$, in accordance with the signals from the receiver controller 6 are selected and added, and the result of the adding operation is displayed in a display 9, such as a waveform display.

The computer 5 incorporates programs for controlling the delay time, which determines the commencement of the conversion of the analog signals to digital signals in the A/D converter 7 and the channels which are selected in the adder 8. The delay times are controlled by the computer 5 in accordance with the steered angles of the ultrasonic wave and the distance of the convergence thereof.

Namely, in the phased array ultrasonic testing equipment, it is possible to control the steered angle of the ultrasonic wave, i.e., the direction of the ultrasonic wave beam, and the divergence thereof by properly setting the above delay time. In the phased array ultrasonic testing equipment mentioned above, it is also possible to scan the ultrasonic wave beam without mechanically moving the probe (transducer elements). This is called an electroscanning method.

Figure 3A:
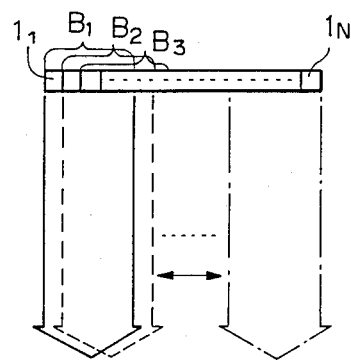
FIGS. 3a and 3b are views showing a known linear scanning method and sector scanning method, respectively.

There are two electroscanning methods, a linear scanning method which the ultrasonic wave beam is scanned by successively actuating transducer blocks B1, B2, ..., each block having a plurality of transducer elements $1_1, 1_2, \ldots 1_n$, in turn, so that the ultrasonic wave beam scans along a straight line as shown in FIG. 3a, and a sector scanning method in which the steered angle of the ultrasonic wave beam by a plurality of transducer $1_1, 1_2, \ldots 1_i$, for example, corresponding to one transducer block B shown in FIG. 3a, is controlled by controlling the delay time, so that the ultrasonic wave beam scans in the form of a sector.

Figure 3B:
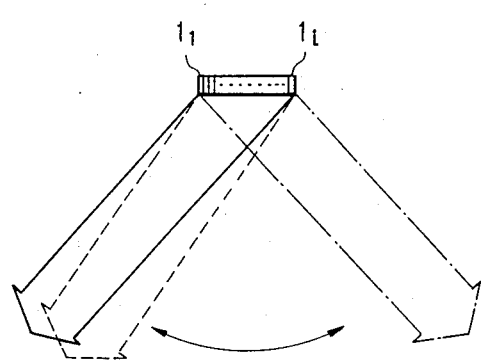
Figure 4A:
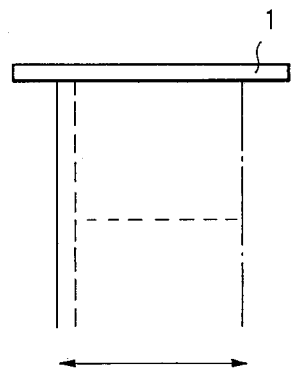
FIGS. 4a and 4b are simplified views of the linear scanning method and the sector scanning method shown in FIGS. 3a and 3b.
Figure 4B:
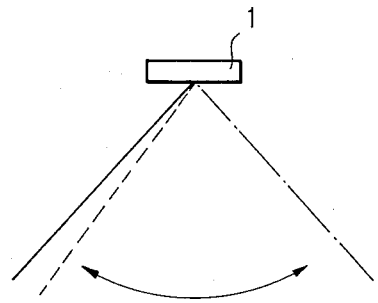

Note that, although the ultrasonic wave beam has a certain width, as shown in FIGS. 3a and 3b, the beam is represented by a single line, which represents a track of a center of the beam as shown in FIGS. 4a and 4b, in the drawings other than FIGS. 3a and 3b, for clarification only.

Figure 5:
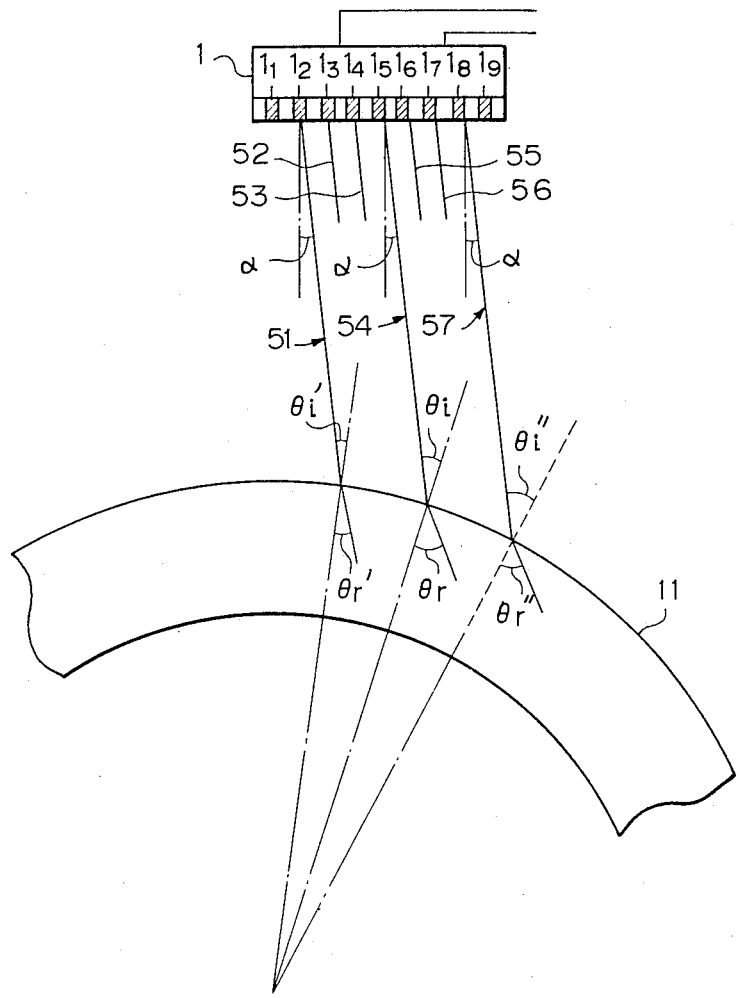
FIGS. 5 and 6 are views showing how flaws in a steel pipe are detected by a linear scanning method.

In the application of the phased array ultrasonic testing equipment to the ultrasonic detection of flaws, the linear scanning method is more generally used as, for example, disclosed in Japanese Unexamined Patent Publication (Kokai) No. 61-18860. FIG. 5 shows a linear scanning method for a ultrasonic flaw detection disclosed in JUPP No. 61-18860. In FIG. 5 which shows the probe 1 having an array of transducer elements $1_1, 1_2, \ldots 1_9$, each transducer block has three adjacent transducer elements.

To scan the ultrasonic wave beam from left to right in FIG. 5, the transducer elements are successively actuated in sequence, and the beams 51 to 57 are successively transmitted and scanned by the transducer blocks. The beams 51 to 57 have the same steered angle $\alpha$. First, the beam 51 emitted by the first transducer block having the transducer elements $1_1, 1_2$ and $1_3$ is passed through the pipe 11 to be tested, and the reflected beam of the beam 51 is received by the first transducer block, then the second beam 52 emitted by the second transducer block having the transducer elements $1_2, 1_3,$ and $1_4$ is passed through the pipe and the reflection beam thereof is received by the second transducer block. The same operation is repeated successively until reaching the last transducer block.

The steered angle of the beam is set in accordance with the refraction angle $\theta r$, the incident angle $\theta i$, which can be determined in accordance with a couplant filling the space between the probe and the pipe 11, and the position of the probe 1. As mentioned before, the steered angle $\alpha$ can be determined by the delay time between the transducer, elements for example, the transducer elements $1_1, 1_2,$ and $1_3$.

If there is no difference in delay time between the transducer blocks, the steered angles of the beams 51 to 57 are identical, as shown in FIG. 5.

However, because the steel pipe 11 has a cylindrical surface, the incident angles $\theta i$ of the beams 51 to 57 are different, and accordingly, the refraction angles $\theta r$ become different. In FIG. 5, the incident angles of the beams 51, 54, and 57 are represented by $\theta i'$, $\theta i$, and $\theta i''$, and the refraction angles thereof by $\theta r'$, $\theta r$, and $\theta r''$, respectively. The following relationship is given between the incident angles and between the refraction angles.

$$\theta i' < \theta i < \theta i'', \theta r' < \theta r < \theta r''$$

Preferably, the beams used for the flaw detection have the same refraction angle, since if the beams have different refraction angles a dispersion of the beams occurs, resulting in a reduced sensitivity of the flaw detection process.

Figure 6:
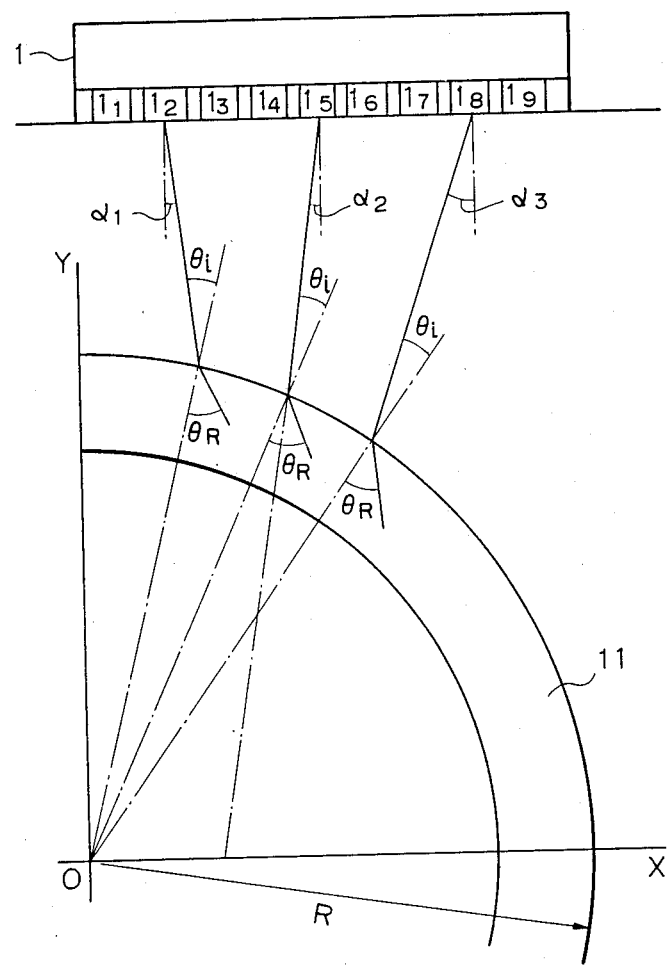

To solve the problem mentioned above, it is known to control the steered angles $\alpha$ of the beams so as to make the incident angles $\theta i$, and accordingly, the refraction angles $\theta r$, of the beams identical. The steered angle can be varied by controlling the delay time of the pulses output to the transducer elements so that the beams 51, 54, and 57 have different steered angles $\alpha_1$, $\alpha_2$, $\alpha_3$, as shown in FIG. 6. The steered angles $\alpha_1$, $\alpha_2$, and $\alpha_3$ (generally $\alpha_i$; i=1, 2, ... n) at which the incident angles, and accordingly, the refraction angles, are constant can be determined in accordance with the geometrical conditions of the steel pipe and the probe; for example, the center position of the probe 1 in an x-y coordinate having a center located on the center 0 of the pipe 11, the inclination angle of the probe with respect to the pipe surface, the number of transducers elements and the pitch of the elements, and the outer diameter of the steel pipe, etc.

However, as mentioned before, the steel pipe does not always have a completely circular cross section. In particular, the UO-pipe tends to be non-circular. Note, the arithmetic process in the computer for determining the steered angles of the ultrasonic wave beams is based on the supposition that the steel pipe has a completely circular cross section. Accordingly, if the pipe is non-circular, the steered angles of the beams are not exact and are deviated from the actual angles.

In addition to the foregoing, especially in an automatic ultrasonic flaw detection process, possible vibration of the steel pipe during the conveyance thereof and foreign material adhering to the surface of the pipe, such as weld-spatter, may have an adverse influence on the preset inclination angle of the probe relative to the pipe surface, resulting in a decrease in the accuracy of the detection process.

When the incident angles $\theta i$ of the ultrasonic wave beams are deviated from the predetermined values, the deviation leads to a large deviation of the refraction angle $\theta r$. This will be explained in more detail below.

According to the Snell Laws of Refraction, when N ultrasonic wave is incident from a first medium having a propagation velocity of C1 upon a second medium having a propagation velocity of C2 at an incident angle of $\theta i$, so that the ultrasonic wave is refracted by the second medium at a refraction angle $\theta r$, the following relationship stands:

$$C1 \cdot \sin\theta r = C2 \cdot \sin\theta i$$

Supposing that the first medium is a couplant mentioned before, which is usually water, and the second medium is a steel, then C1=1480 m/s and C2 =3230 m/s.

Therefore, supposing that $\theta i = 25.5°$, $\theta r = 70°$ stands.

If the incident angle $\theta i$ changes by 1° to 26.5°, the refraction angle $\theta r$ becomes 76.9° ($\theta r = 76.9°$). As can be seen from this result, a change of the incident angle by 1° causes a deviation of the refraction angle of 6.9°, so that the refracted beam may move out of a desired detection area, such as a welded portion of the UO-pipe.

Figure 7A:
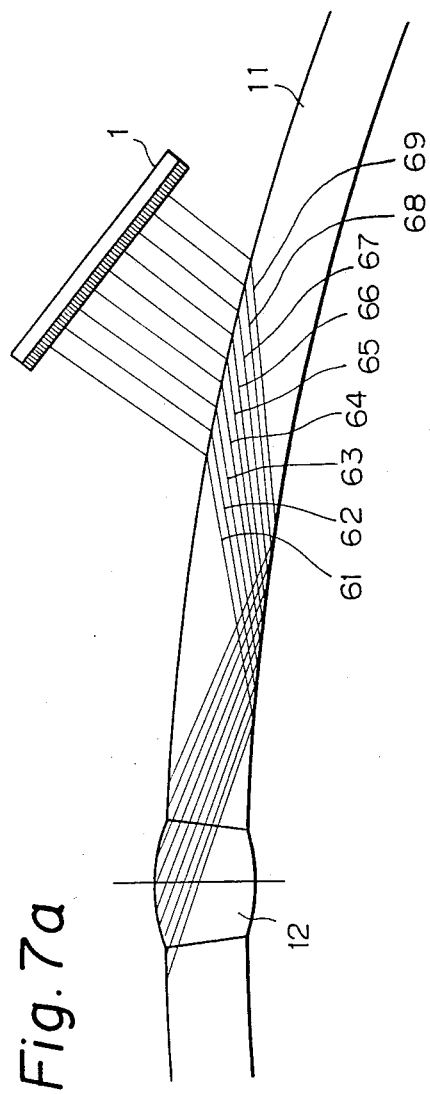
FIG. 7a is a view showing one example of paths of ultrasonic wave beams which accurately reach a target portion to be tested; and, FIG. 7b is a view similar to FIG. 7a but showing deviations of the ultrasonic wave beams.
Figure 7B:
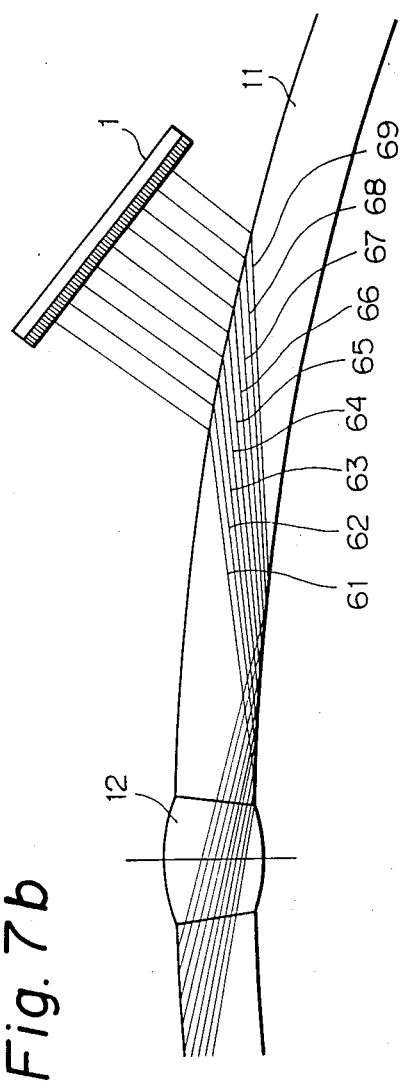

FIGS. 7a and 7b show pats of the ultrasonic wave beams in an ultrasonic flaw detection process for detecting an upper portion of the welded portion 12 close to the outer periphery of the pipe 11 by the method shown in FIG. 6. In FIG. 7a, the refracted beams 61 to 69 accurately reach the intended upper portion of the welded portion 12 of the pipe 11. On the contrary, in FIG. 7b, the incident angle changes by 0.5° in comparison with FIG. 7a, so that the refracted beams 61 to 69 move out of the upper portion of the welded portion 12 to be tested.

The primary object of the present invention is to eliminate the drawbacks mentioned above. Namely, the present invention is aimed at a realization of a precise ultrasonic flaw detection even if the pipe to be tested has a non-circular cross section, or the inclination of the probe 1 is deviated from a predetermined value.

To eliminate the drawbacks mentioned above, according to the present invention, a fluctuation of the direction of the propagation of the ultrasonic wave beam due to the irregularity of the surface of the pipe and the inclination of the probe is always monitored to detect ultrasonic wave beams which reach the target portion (welding portion) of the pipe.

Figure 1A:
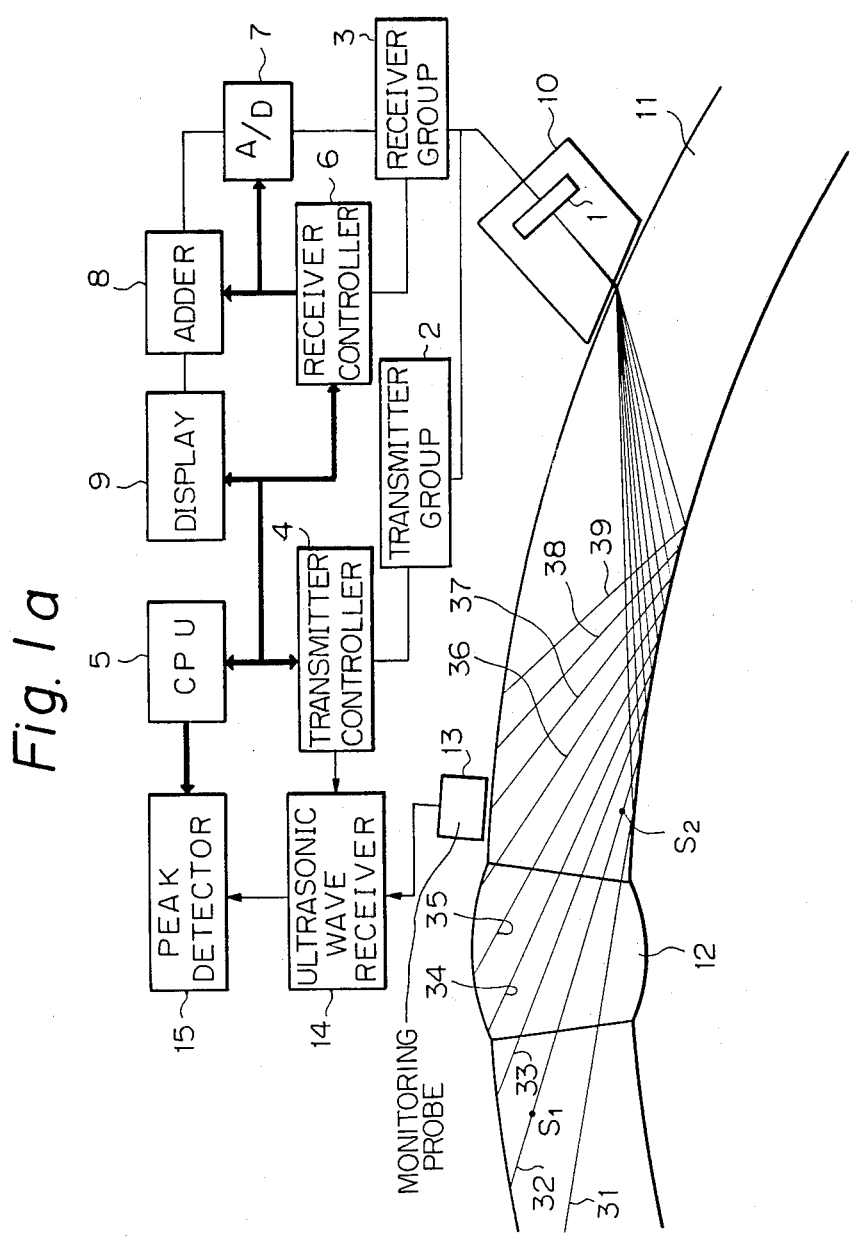

FIGS. 1a to 1i show embodiments of the present invention. In FIG. 1a, the probe 1 having an array of transducer elements $1_1, 1_2, \ldots 1_i$ (FIG. 3a) is coupled to a couplant (not shown), such as water, by a coupling device 10. As is well known, the couplant with which the space between the probe 1 and the pipe 11 is filled eliminates air which would otherwise exist in the space between the probe 1 and the pipe 11 and which would largely refract the ultrasonic wave beam transmitted from the probe 1.

Figure 1B:
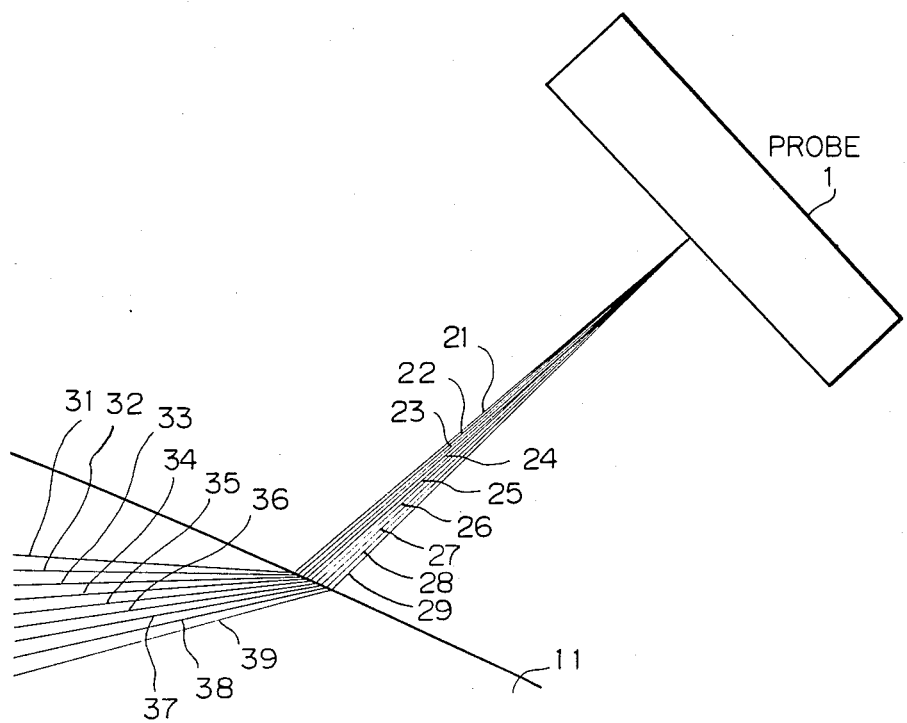

FIG. 1b shows an enlarged view of the ultrasonic wave beam transmitted from the probe 1 shown in FIG. 1a to the pipe 11.

The probe 1 transmits ultrasonic wave beams 21 to 29 in a sector scanning fashion as shown in FIG. 3b, in accordance with the commands of the computer 5, which are based on preset conditions, such as the diameter and thickness of the pipe 11, the position and inclination of the probe 1, and the angles of incidence of the ultrasonic wave beams emitted from the probe 1, etc. In the sector scanning, the beams are scanned over a relatively wide range. Namely, as can be seen from FIG. 1a the scanned refracted beams 31 to 39 corresponding to the beams 21 to 29 reach the upper portion of the welded portion 12 of the pipe and wide areas adjacent to the welded portion 12 on the opposite sides thereof, so that in the illustrated embodiment, the beams 31, 32, and 33 reach the left side area of the welded portion 12 and the beams 37, 38 and 39 reach the right side area of the welded portion 12, respectively. Therefore, the beams 37, 38, and 39, and some of the beams 31, 32, and 33 are unable to detect a flaw in the upper portion of the welded portion 12, in a state shown in FIG. 1a in which there is no deviation of the angles of incidence of the ultrasonic wave beams.

When the beams 21 to 29 are incident upon the pipe 11, they are refracted by the pipe 11 in accordance with Snell Laws of Refraction, to become the beams 31 to 39. The refraction angles of the beams 21 to 29 fluctuate depending on the surface profile of the pipe and the inclination of the probe 1, etc. The refracted beams 31 to 39 propagate in the pipe 11 and the welded portion 12. If there is a flaw in the pipe or the welded portion 12, the reflected beams are reflected by the flaw, and the reflected beams are received by the probe 1 to detect the flaw.

In the present invention, the flaws to be detected are mainly those in the welded portion 12, although not limited thereto. This is because, generally, flaws in portions other than the welded portion are detected before the blank plate is bent into a UO pipe-shape, as mentioned before.

The reflected beams from the flaw in the welded portion can be detected in the same way as mentioned above with reference to FIG. 2, wherein the receiving of the reflected beams by the probe 1 is also effected in a sector scanning method.

However, in the detection operation by the sector scanning method, since the refraction angles of the beams vary in accordance with the surface profile of the pipe 11 and the inclination angle of the probe 1, there is no guarantee that the ultrasonic wave beams will propagate in the pipe along the designed or intended paths.

To confirm the propagation of the beams, according to the present invention, a monitoring probe 13 for receiving the beams is located in the vicinity of the welded portion 12. The monitoring probe 13 is electrically connected to an ultrasonic wave receiver 14 which is connected to the transmitter controller 4 and which successively receives the beams 31 to 39 in accordance with control signals from the transmitter controller 4 at a proper timing. The beam paths can be calculated from the geometrical arrangement of the array probe 1 and the monitoring probe 13.

First, the beam 31 is transmitted from the probe 1 in response to the transmitted pulse of the transmitter unit 2, in accordance with control signals from the transmitter controller 4, which is driven in response to control signals from the computer 5. Since the probe 1 transmits and receives the ultrasonic wave beams, the receiver controller 6 is driven in response to the control signals from the computer 5, simultaneously with the drive of the transmitter controller 4 or with a delay time which is predetermined by taking the time needed by the reflected beams to return to the probe 1 into consideration.

For all ultrasonic wave beams, e.g., the beam 32, the transmitter controller 4 is energized by a drive pulse, and, at the same time or thereafter the receiver controller 6 is energized by a drive pulse with a predetermined pulse width $w_0$ which corresponds to time between the points $S_1$ and $S_2$ (FIG. 1a) which are located on the opposite sides of the welded portion 12, for example, with a predetermined delay time $t_0$, shown in FIG. h. The delay time $t_0$ can be determined in accordance with the time needed for the beams to return to the probe 1. The delay time can be zero. The pulse width $w_0$ of the drive pulse of the receiver controller 6 can be determined in accordance with the paths of the beams in the pipe. Namely, it is sufficient to detect only the sections of the beams which cover the welded portion 12 and the vicinity thereof in order to detect a flaw in the welded portion 12. That is, only the signals within a predetermined gate are detected.

When a flaw exists in the welded portion 12, the reflected beam shows an echo, as shown in FIG. 1h.

A peak detector 15 detects peak values of each of the beams 31 to 39 within the predetermined gate and the detected data is input to the computer 5.

Since the computer 5 controls the transmitter controller 4, as mentioned above, the data of the peak values detected by the peak detector corresponds to the beams 31 to 39.

When the peak values are detected by the peak detector 15, the detection can be effected for signals within a predetermined gate, similar to the detection of the flaw. Namely, the signals of the ultrasonic beams in the vicinity of the points thereof intersecting at the outer surface of the pipe 11 can be detected.

Figure 1E:
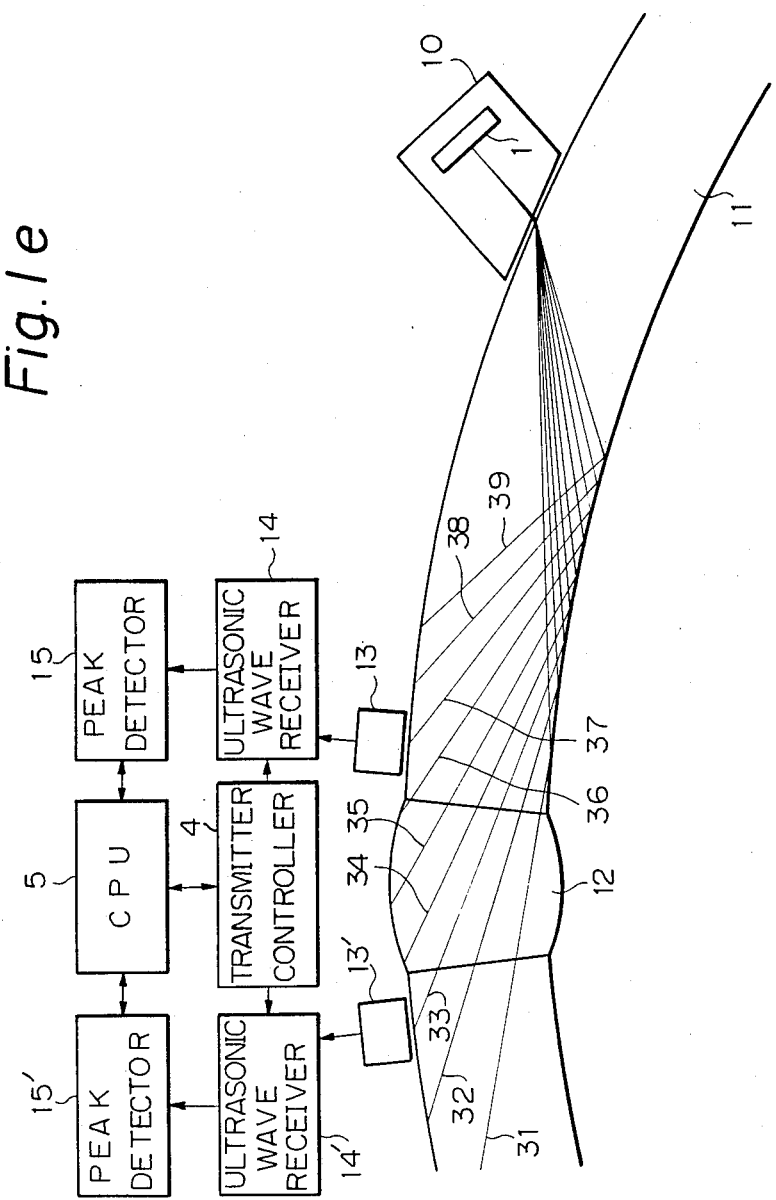
Figure 1G:
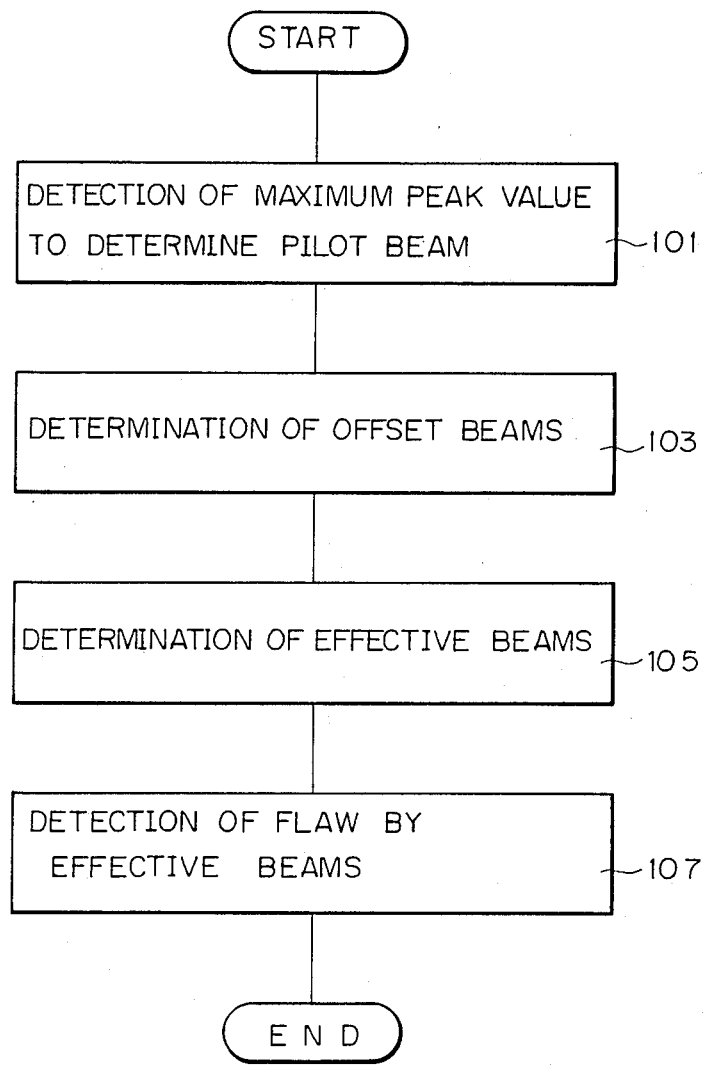

In the computer 5, at step 101 shown in FIG. 1g, the peak values of the beams 31 to 39 are compared to detect a maximum peak value. The maximum peak value corresponds to a beam closest to the monitoring probe 13. In the embodiment illustrated in FIG. 1a, the beam 37 has the maximum peak value.

The beam having the maximum peak value is referred to as a pilot beam herein. Namely, in the illustrated embodiment, the beam 37 is a pilot beam. After that, at step 103, a beam which reaches the upper portion of the welded portion 12 of the pipe and which is furthest from the pilot beam can be determined from the pilot beam. This furthest beam is referred to as an offset beam herein. Namely, since the data of the positional relationship between the probe 1 and the pipe 11, the scanning pitch of the beams in the sector scanning method, and the outer diameter and the thickness of the pipe 11 etc. is stored in advance in the computer 5, it is possible to presume the paths of the beams from that data. That is, by using the pilot beam as a reference, it is possible to determine the offset beam. Then, at step 105, the effective beams, which are between the pilot beam and the offset beam and which reach the upper portion of the welded portion 12 of the pipe 11, are determined. In the embodiment illustrated in FIG. 1a, the offset beam is the beam 33, and the effective beams are the beams 34, 35, and 36. The number of the effective beams is three in the illustrated embodiment. Finally, when the effective beams are selected, the flaw detection can be effected by only using the data of the effective beams.

It is possible to include the offset beam among the effective beams. That is, in this concept, the offset beam 33 is one of the effective beams. Furthermore, it is also possible to optionally define the offset beam. Note that all of the beams between the offset beam and the pilot beam are not always effective beams, depending on the selection of the offset beam and the pilot beam. For example, in FIG. 1a, if the monitoring probe 13 was located in the vicinity of the beam 38, the beam 38 would be the pilot beam. In this case, the beam 37 is not an effective beam. Namely, only some of the beams between the pilot beam and the offset beam may be determined to be effective beams.

Generally speaking, in the sector scanning method for testing a pipe, the points of incidence of the ultrasonic wave beams on the pipe can be considered substantially constant, as shown in FIG. 1a, and accordingly, it can be assumed that the deviation of the direction (refraction angle) of the beams due to the irregularity of the pipe and the change of the inclination of the probe 1 takes place for all beams with the same tendency. Therefore, according to the present invention, in which the effective beams which can be used to detect the flaw are determined from the data of the monitoring probe 13, a very precise detection can be expected.

The monitoring probe 13 can be either directional or nondirectional. When a directional probe, which is directional to the receiving of the beams, is used, the angles of the beams to be received are determined in accordance with the positions of the array probe 1 and the monitoring probe 13, and the diameter and the thickness of the pipe 11. Accordingly, when an angle probe is used, the inclination of the transducers can be predetermined in accordance with the angles of the beams. When an array probe is used, the delay time for controlling the ultrasonic wave beams can be predetermined in accordance with the angles of the beams.

FIG. 1c shows a position in which the inclination of the array probe 1 deviates by +0.5° in comparison with the position shown in FIG. 1a. FIG. 1c, the pilot beam is the beam 38, and the offset beam is the beam 34. The effective beams are the beams 35, 36, and 37. Accordingly, in the embodiment shown in FIG. 1c, the data of the three effective beams 35, 36, and 37 is used to detect the flaw in the upper portion of the welded portion 12 of the pipe 11.

FIG. 1d shows a position in which the inclination of the probe 1 deviates by −0.5°, in comparison with the position shown in FIG. 1a. In FIG. 1d, the beam 36 is the pilot beam, and the beam 31 is the offset beam. The effective beams are the beams 32, 33, 34, and 35. These four effective beams are used to detect the flaw in the upper portion of the welded portion 12 of the pipe 11.

The monitoring probe 13 and the array probe 1 are independently coupled to the respective couplant, such as water, in the illustrated embodiment. Alternatively, it is possible to couple both of the probes to a common couplant. Namely, in this alternative, the probes 1 and 13 are located, for example, in a water reservoir 50, as shown by an imaginary line 50 in FIG. 1c.

It is also possible to combine the sector scanning method and the linear scanning method. Namely, an array of a larger number of transducer elements $1_1$, $1_2$ ... $1_n$ is provided and is divided into several blocks $B_1$, $B_2$, $B_3$, ..., as shown in FIG. 3a, so that the blocks are successively actuated, as mentioned with reference to FIG. 3a. The combination of the sector scanning method and the linear scanning method contributes to an increase of the density of the detection of weld flaws in the pipe, although a longer time is needed to complete the detection process.

FIG. 1e shows another embodiment of the present invention, in which two monitoring probes 13 and 13' are provided in the vicinity and on opposite sides of the welded portion 12 of the pipe 11. The additional monitoring probe 13' is connected to an ultrasonic wave receiver 14' similar to the ultrasonic wave receiver 14, and the receiver 14' is connected to a peak detector 15' similar to the peak detector 15 connected to the computer 5. In FIG. 1e, the circuit arrangement is same as that of FIG. 1a, except for the addition of the additional probe 13', the additional ultrasonic wave receiver 14' and the additional peak detector 15' The additional monitoring probe 13', the ultrasonic wave receiver 14', and the peak detector 15' are used to detect peak values of the beams 31 to 39, similar to the detection of the peak values by the probe 1 and the peak detector 15, etc., associated therewith, as mentioned before.

Figure 1I:
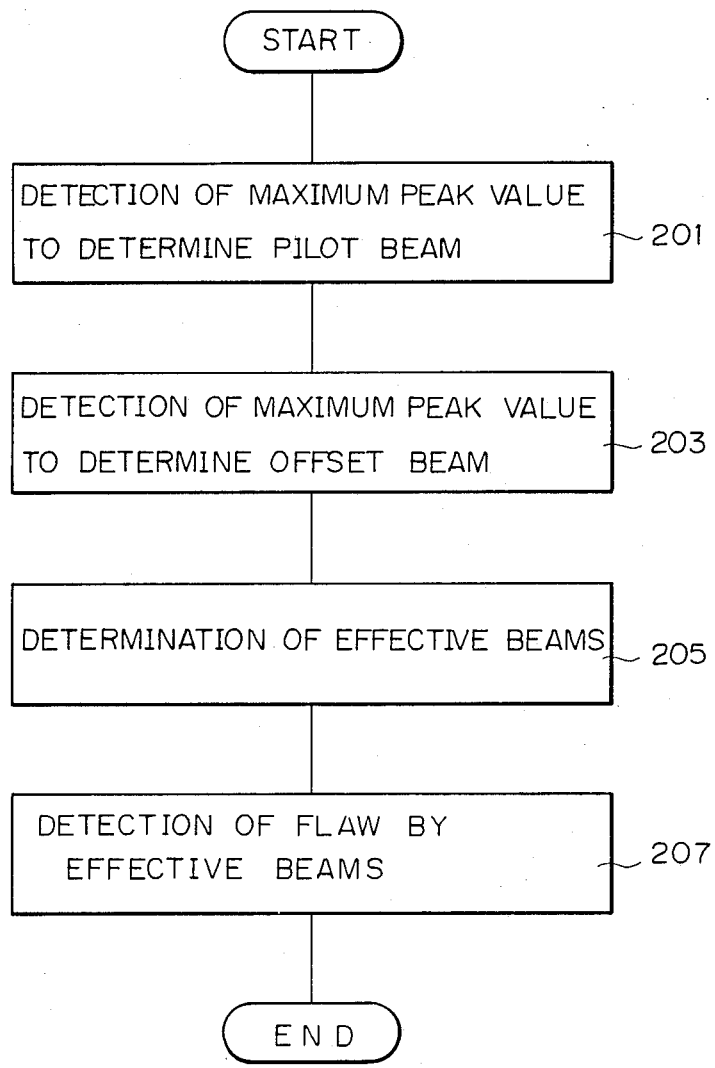

FIG. 1i is a flow chart of the operation of the computer 5 for the arrangement shown in FIG. 1e. In FIG. 1i, the maximum peak value of the peak values detected by the peak detector 15 is detected at step 201 to determine the pilot beam, similar to FIG. 1g. At step 203, the maximum peak value of the peak values of the beams 31 to 39 detected by the peak detector 15' is detected to determine the offset beam. Namely, the offset beam is detected by the additional monitoring probe 13', the additional ultrasonic wave receiver 14', and the additional peak detector 15' in the embodiment shown in FIG. 1e, unlike the embodiment shown in FIG. 1a in which both the pilot beam and the offset beam are detected by the data from the monitoring probe 13, as mentioned above.

In the arrangement shown in FIG. 1e, the beam 33 is the offset beam.

Then, at step 205, the effective beams are determined from the pilot beam and the offset beam. Namely, the beams between the pilot beam and the offset beam are determined to be effective beams. In the illustrated embodiment, the beams 34, 35, and 36 are the effective beams.

Finally, at step 207, the flaw in the upper portion of the welded portion 12 of the pipe 11 is detected by using only the data of the thus determined effective beams.

As can be determined from the above description, it is possible to provide only the monitoring probe 13' and omit the probe 13, to achieve the object of the present invention. Namely, it is possible to locate one monitoring probe 13' on the opposite side of the welded portion 12 to the location of the monitoring probe 13 shown in FIG. 1a.

The above discussion has been directed to the detection of flaws in the upper portion of the welded portion 12 of the pipe 11 but, when a flaw in the lower portion of the welded portion 12 of the pipe is to be detected, the arrangement illustrated in FIG. 1f can be used. In FIG. 1f the monitoring probe 13 is provided in the vicinity of the welded portion 12 on the opposite side of the welded portion 12 (i.e., on the left side of the welded portion 12 in FIG. 1f) to the location of the monitoring probe 13 in FIG. 1a, in which the monitoring probe 13 is located on the right side of the welded portion 12. Namely, the probe 13 and the probe 1 are located on opposite sides of the welded portion 12 in FIG. 1f, contrary to the arrangement of FIG. 1a in which the probe 1 and probe 13 are located on the same side of the welded portion 12.

In FIG. 1f, the refraction angles of the transmitted ultrasonic wave beams 41 to 49 are different from those of the beams shown in FIG. 1a. Further, in the embodiment shown in FIG. 1f, the beams 47 and 43 are the pilot beam and the offset beam, respectively, and the beams 44, 45 and 46 are effective beams.

Note, particularly when a pipe is to be tested, it is very difficult to arrange the probes 1, 13 and 13' within the pipe, and accordingly, the probes are preferably provided outside the pipe.

According to the present invention, as can be understood from the above discussion, since the fluctuation of the directions (refraction angles) of the ultrasonic wave beams propagating in the pipe can be always monitored by the monitoring probe or probes, the beams which actually reach the portion of the pipe that is to be tested can be determined by the data from the monitoring probe or probes. As a result, a flaw in that portion of the pipe can be detected with a high accuracy, resulting in an increased reliability of the welded portions of the pipe.

We claim:

1. An ultrasonic flaw detecting method for ultrasonically detecting flaws in a portion of a subject to be tested by using an ultrasonic wave phased array probe having an array of a plurality of transducers for emitting and receiving ultrasonic wave beams in a sector scanning fashion in which the beams are scanned substantially in the form of a sector, and wherein at least one monitoring probe is located in the vicinity of the portion of the subject that is to be tested to receive the ultrasonic wave beams, comprising detecting peak values of the ultrasonic wave beams within a predetermined gate, determining a maximum peak value of the detected peak values to determine a pilot beam having the maximum peak value, determining from the determined pilot beam effective beams which reach the portion of the subject to be tested, so that the detection of the flaws can be effected by using only the effective beams.

2. A method according to claim 1, further comprising determining an offset beam which can be used as a reference beam for determining the effective beams, after the pilot beam is determined.

3. A method according to claim 2, wherein said effective beams are determined to be beams between the pilot beam and the offset beam.

4. A method according to claim 1, wherein said portion of the subject to be tested is a welded portion of a pipe.

5. An ultrasonic flaw detecting apparatus for ultrasonically detecting flaws in a portion of a subject to be tested by using an ultrasonic wave phased array probe having an array of a plurality of transducers for emitting and receiving ultrasonic wave beams in a sector scanning fashion in which the beams are scanned substantially in the form of a sector, comprising a monitoring probe which is located in the vicinity of the portion of the subject to be tested to receive the ultrasonic wave beams;

means for detecting peak values of the ultrasonic wave beams within a predetermined gate;

means for determining a maxium peak value of the detected peak values to determine a pilot beam having the maxium peak value; and means for determining effective beams which reach the portion of the subject to be tested from the determined pilot beam.

6. An apparatus according to claim 5 further comprising means for determining an offset beam which can be used as a reference beam for determining the effective beam.

7. An apparatus according to claim 5, wherein said effective beams are beams between the pilot beam and the offset beam.

8. An apparatus according to claim 5, further comprising an additional monitoring probe which is located in the vicinity of the portion of the subject to be tested, for receiving the ultrasonic wave beams.

9. An apparatus according to claim 8, wherein said additional monitoring probe is located on an opposite side of the portion of the subject to be tested, to the first mentioned monitoring probe.

10. An apparatus according to claim 5, wherein said portion of the subject to be tested is a welded portion of a pipe.

* * * * *

UNITED STATES PATENT AND TRADEMARK OFFICE
CERTIFICATE OF CORRECTION

PATENT NO. : 4,821,575
DATED : April 18, 1989
INVENTOR(S) : Y. Fujikake, et al.

It is certified that error appears in the above-identified patent and that said Letters Patent is hereby corrected as shown below:

Column 3, line 34, after "transmitters" insert a period.

Column 6, line 3, change "pats" to --paths--.

Column 7, line 2, change "reflected" to --refracted--.

Column 7, line 53, change "FIG. h." to --FIG. 1h.--.

Column 9, line 12, before"FIG. 1c,"insert --In--.

Column 12, line 8, change "maxium" to --maximum--.

Column 12, line 10, change "maxium" to --maximum--.

Signed and Sealed this

Eighth Day of August, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,821,575
DATED : April 18, 1989
INVENTOR(S) : Yoichi Fujikake et al It is certified that error appears in the above-identified patent and that said Letters Patent is hereby corrected as shown below:

On the title page assignee should read

--(73) Assignee: Nippon Steel Corporation, Chiyoda, Japan
Kabushiki Kaisha Toshiba, Kanagawa, Japan--.

Signed and Sealed this

Thirteenth Day of March, 1990

*Attest:*

JEFFREY M. SAMUELS

*Attesting Officer*     *Acting Commissioner of Patents and Trademarks*

UNITED STATES PATENT AND TRADEMARK OFFICE
CERTIFICATE OF CORRECTION

PATENT NO.   :   4,821,575
DATED        :   April 18, 1989
INVENTOR(S)  :   Y. Fujikake et al.

It is certified that error appears in the above-identified patent and that said Letters Patent is hereby corrected as shown below:

On page 1, under the heading [73] Assignee:, add

-- Kabushiki Kaisha Toshiba, Kanagawa, Japan and

Krautkramer Foerster Japan Co., Ltd., Tokyo, Japan --.

This Certicate supercedes Certificate of Correction issued March 13, 1990.

Signed and Sealed this

Fourth Day of December, 1990

Attest:

HARRY F. MANBECK, JR.

*Attesting Officer*     Commissioner of Patents and Trademarks